United States Patent [19]

Sano et al.

[11] Patent Number: 4,757,009

[45] Date of Patent: Jul. 12, 1988

[54] RECOMBINANT DNA HAVING A PHOSPHOENOL PYRUVATE CARBOXYLASE GENE INSERTED THEREIN, BACTERIA CARRYING SAID RECOMBINANT DNA AND A PROCESS FOR PRODUCING AMINO ACIDS USING SAID BACTERIA

[75] Inventors: Konosuke Sano, Tokyo; Koichi Ito, Kawasaki; Kiyoshi Miwa, Matsudo; Shigeru Nakamori, Yokohama, all of Japan

[73] Assignee: Ajinomoto Co., Inc., Tokyo, Japan

[21] Appl. No.: 645,107

[22] Filed: Aug. 28, 1984

[30] Foreign Application Priority Data

Aug. 29, 1983 [JP] Japan ................................ 58-157512

[51] Int. Cl.[4] ........................ C12P 13/04; C12P 13/20; C12N 15/00; C12N 1/20; C12N 1/00; C12R 1/13; C12R 1/15
[52] U.S. Cl. ................................... 435/106; 435/109; 435/172.3; 435/253; 435/320; 435/840; 435/843; 935/14; 935/29; 935/60; 935/72
[58] Field of Search ............... 435/106, 107, 109, 110, 435/114, 115, 116, 172.3, 253, 317, 232, 840, 843

[56] References Cited

FOREIGN PATENT DOCUMENTS 0058889 9/1982 European Pat. Off. ...... 435/172.3 X

OTHER PUBLICATIONS

Izui, K. et al., *Febs Letters*, vol. 133, No. 2, pp. 311–315, 1981.
Ishijima, S. et al., *J. Gen. Applied Micriol*, vol. 30, pp. 27–33, 1984.
Sabe, H. et al., *Gene*, vol. 31, pp. 279–283, 1984.
Fujita, N. et al., *J. Biochem*, vol. 95, pp. 909–916, 1984, Jun.

*Primary Examiner*—Thomas G. Wiseman
*Assistant Examiner*—Jayme A. Huleatt
*Attorney, Agent, or Firm*—Oblon, Fisher, Spivak, McClelland & Maier

[57] ABSTRACT

A recombinant DNA molecule comprising a plasmid vector having operationally inserted therein a gene coding for phosphoenol pyruvate carboxylase is disclosed along with bacteria containing this recombinant DNA molecule and methods of using these bacteria to produce amino acids in large quantities.

7 Claims, 7 Drawing Sheets

RECOMBINANT DNA HAVING A PHOSPHOENOL PYRUVATE CARBOXYLASE GENE INSERTED THEREIN, BACTERIA CARRYING SAID RECOMBINANT DNA AND A PROCESS FOR PRODUCING AMINO ACIDS USING SAID BACTERIA

BACKGROUND OF THE INVENTION

1. Field of the Invention

The present invention relates to recombinant DNA having inserted therein a gene coding for phosphoenol pyruvate carboxylase, to bacteria carrying the recombinant DNA and to a process for producing amino acids using the bacteria.

2. Description of the Prior Art

Phosphoenol pyruvate carboxylase (4.1.1.31 phosphoenol pyruvate carboxylase; hereafter referred to as "PEPC") is an enzyme which catalyzes the reaction of adding 1 mole of carbon dioxide to phosphoenol pyruvic acid, thereby forming oxaloacetic acid. As such, it plays an extremely important role in supplying aspartic acid by metabolic processes. Accordingly, phosphoenol pyruvate carboxylase also plays an important role in the production of amino acids, such as lysine, threonine, isoleucine, etc., which are formed from aspartic acid. In addition, phosphoenol pyruvate carboxylase plays an important role in the production of amino acids formed from TCA-cycle organic acids (that is, amino acids such as glutamic acid, glutamine, proline, arginine, citrulline, ornithine, etc.) from the oxaloacetic acid that is formed by adding carbon dioxide to phosphoenol pyruvic acid.

SUMMARY OF THE INVENTION

Accordingly, it is an object of this invention to provide a method of increasing the production of amino acids using phosphoenol pyruvic carboxylase.

This and other objects of the invention as will hereinafter become more readily apparent have been accomplished by providing a recombinant DNA molecule comprising a plasmid vector and a gene coding for phosphoenol pyruvic carboxylase operationally inserted therein, wherein said plasmid vector is capable of propagating and said gene is capable of being expressed in a Corynebacterium or Brevibacterium bacterium. Also disclosed as part of the present invention are bacterial transformants containing said recombinant DNA and a process for producing an amino acid using said bacteria.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DESCRIPTION OF THE PREFERRED EMBODIMENTS

Figure 1:
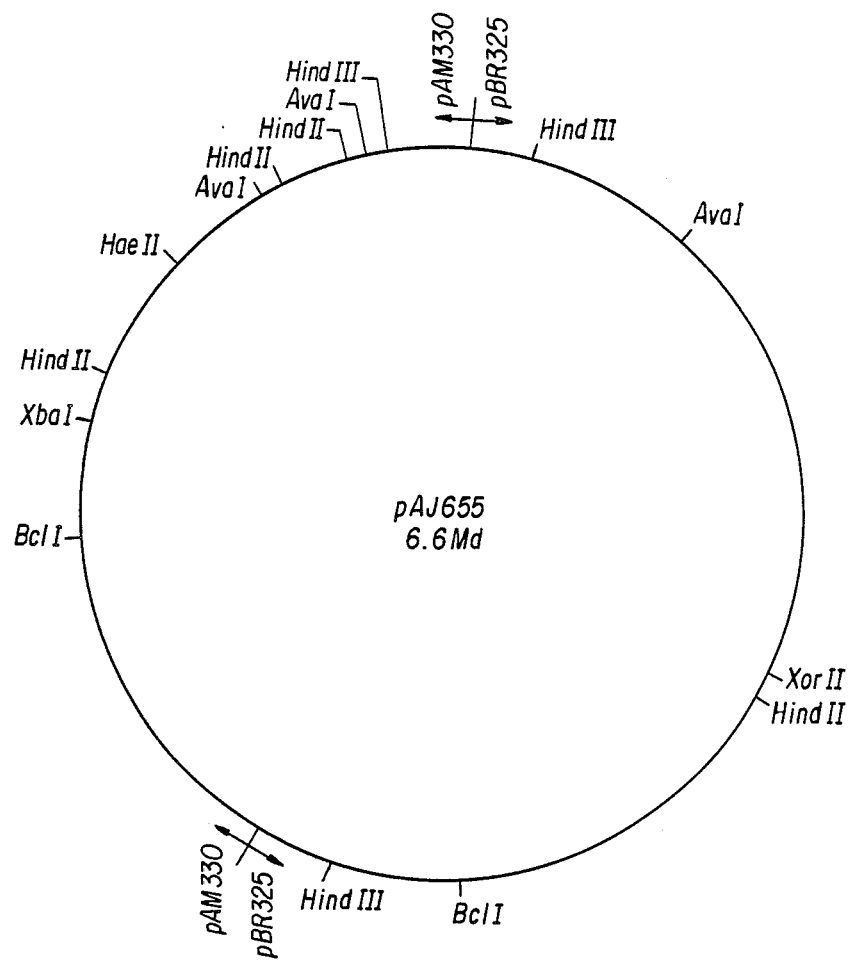
FIG. 1 is a restriction map of composite plasmid pAJ 655.

The present inventors started their investigations with an attempt to amplify PEPC genes in cells of bacteria which are known to produce high amounts of amino acids, e.g., in cells of *Corynebacterium glutamicum* or *Brevibacterium flavum*. Ultimately, the present inventors suceeded in obtaining a recombinant DNA comprising a plasmid vector and a gene coding for PEPC from cells of Corynebacterium and Brevibacterium bacteria along with Corynebacterium and Brevibacterium bacteria carrying the recombinant DNA. Cultivation of such bacteria results in production of markedly high amounts of amino acids excreted into the culture medium.

Coryneform bacteria are aerobic, Gram-positive rods, are non-acid-fast, and are described in Bergey's *Manual of Determinative Bacteriology*, 8th Edition, 599 (1974). Brevibacterium bacteria are described in the same manual and are also Gram-positive, non-acid-fast rods and are aerobic to facultatively anaerobic. These two genera include known wild strains producing L-glutamic acid in a large amount, particular examples of which are shown below:

*Brevibacterium divaricatum* ATCC 14020
*Brevibacterium saccarolyticum* ATCC 14066
*Brevibacterium immariophilum* ATCC 14068
*Brevibacterium lactofermentum* ATCC 13869
*Brevibacterium roseum* ATCC 13825
*Brevibacterium flavum* ATCC 13826
*Brevibacterium thiogenitalis* ATCC 19240
*Corynebacterium acetoacidophilum* ATCC 13870
*Corynebacterium acetoglutamicum* ATCC 15806
*Corynebacterium callunae* ATCC 15991
*Corynebacterium glutamicum* ATCC 13032 and 13060
*Corynebacterium lilium* ATCC 15990
*Corynebacterium melassecola* ATCC 17965
*Corynebacterium ammoniaphilum* ATCC 15354

Corynebacterium and Brevibacterium bacteria also include, in addition to the aforesaid strains having glutamic acid productivity, mutants which produce amino acids such as lysine, arginine, etc.

Isolation of the PEPC gene can be conducted, for example, by the following method. Although the following example refers only to Coryneform bacteria for simplicity, it is to be recognized that Brevibacterium bacteria can likewise be used at any or all points in the procedure. Firstly, a chromosomal gene is extracted from a Coryneform strain carrying a healthy PEPC gene (there can be utilized, for example, the method of H. Saito and K. Miura, *Biochem. Biophys. Acta*, 72, 619 (1963)). The gene is cleaved with an appropriate restriction enzyme and then connected with a plasmid vector capable of propagating in Coryneform bacteria. A PEPC-deficient mutant of Coryneform bacteria is transformed with the resulting recombinant DNA. Bacterial strains which come to possess PEPC-forming activity are isolated, and a PEPC gene can be isolated therefrom.

Preferred donors of the PEPC gene are strains which exhibit weakened feedback inhibition by aspartic acid.

Such strains are recognized as being bacteria resistant to aspartic acid-antagonistic inhibitors.

To cleave chromosomal genes, a wide variety of restriction enzymes can be employed by controlling the degree of cleavage, for example, by controlling the time of the cleavage reaction, the temperature, etc. Cleavage of DNA by restriction enzymes is well understood by those skilled in the art and need not be set forth here in detail.

Figure 2:
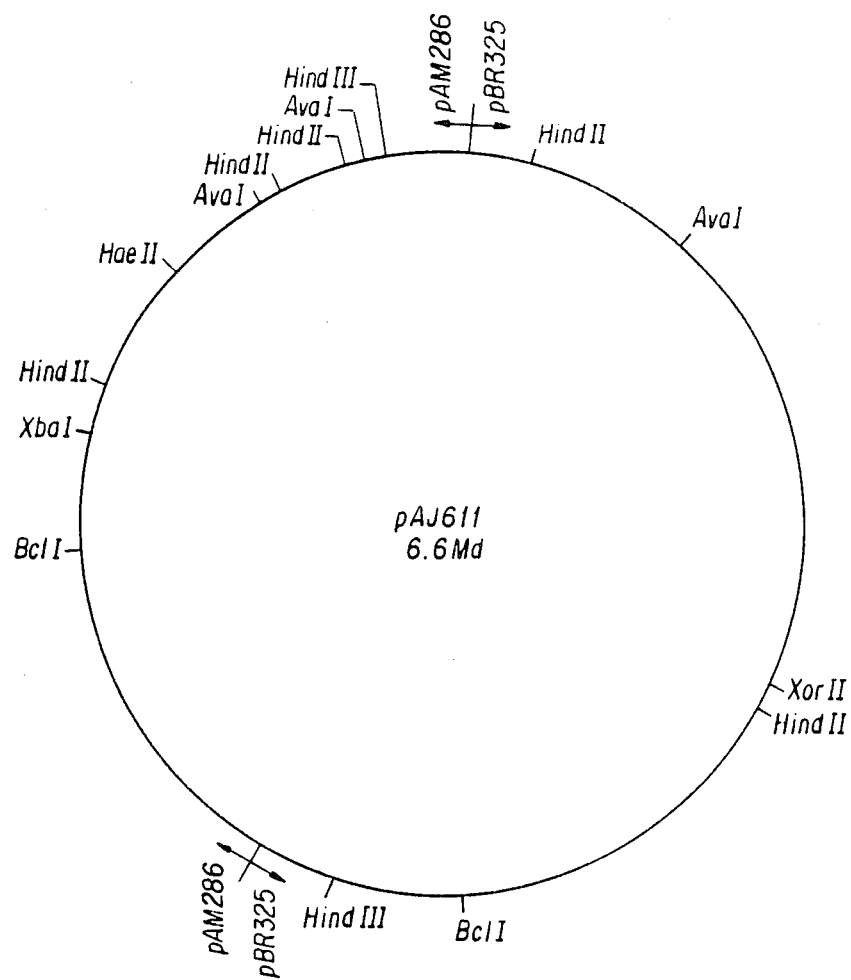
FIG. 2 is a restriction map of composite plasmid pAJ 611.
Figure 3:
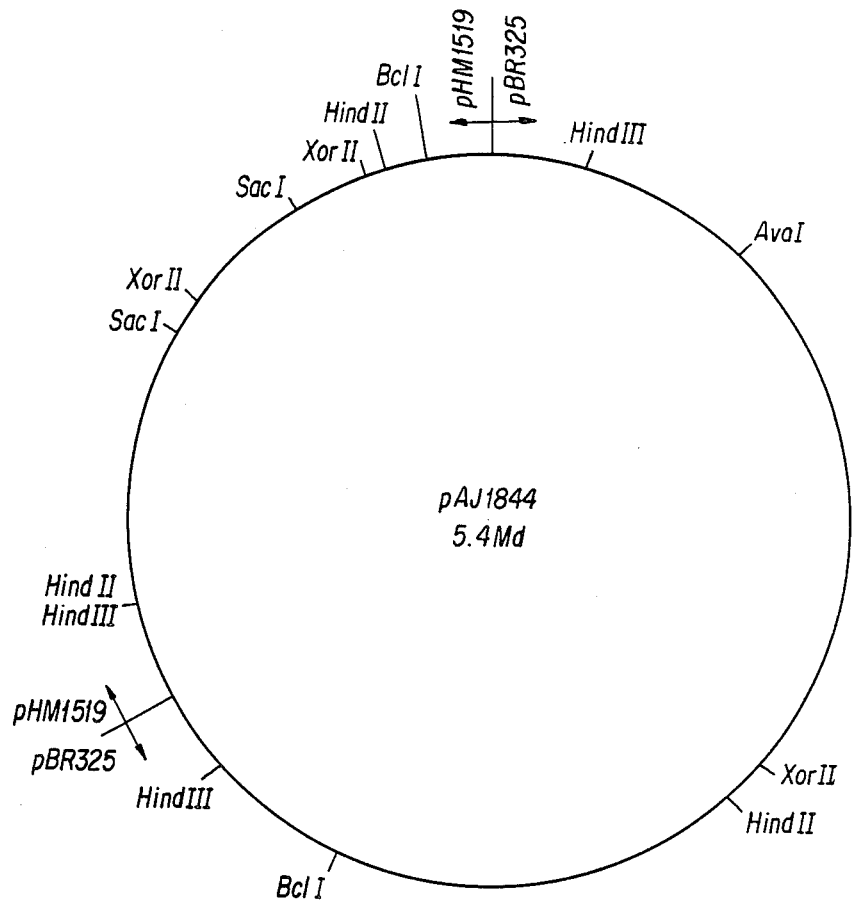
FIG. 3 is a restriction map of composite plasmid pAJ 440.
Figure 4:
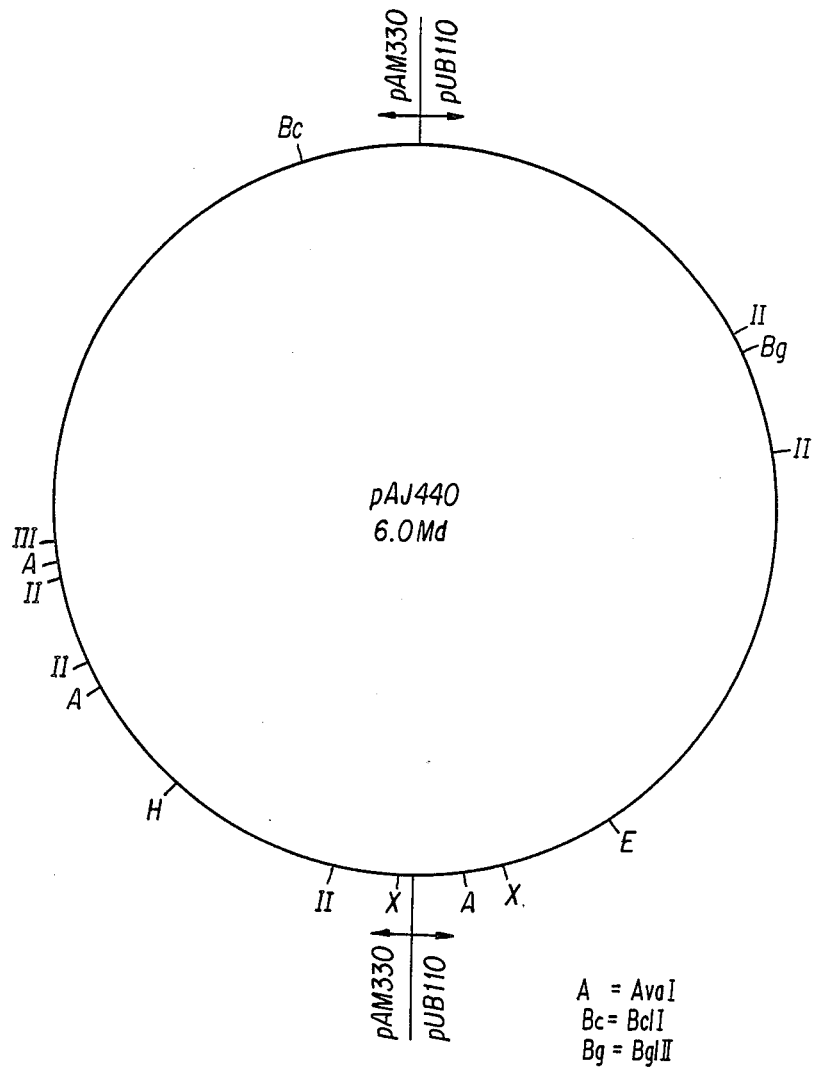
FIG. 4 is a restriction map of composite plasmid pAJ 1844.
Figure 5:
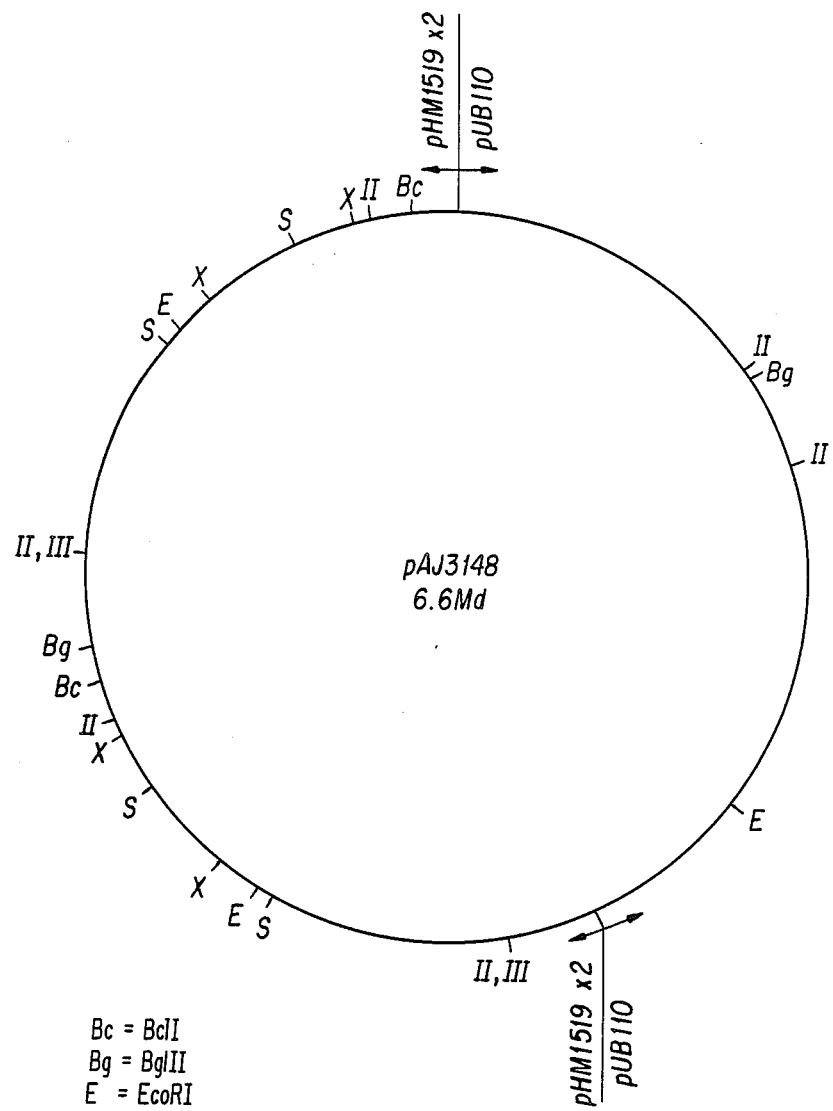
FIG. 5 is a restriction map of composite plasmid pAJ 3148.

The plasmid vector used in the present invention can be any vector as long as it can be propagated in cells of Coryneform or Brevibacterium bacteria. Specific examples include the following:

(1) pAM 330: see Japanese Published Unexamined Patent Application No. 58-67699;
(2) pHM 1519: see Japanese Published Unexamined Patent Application No. 58-77895; (3) pAJ 655:
  (a) host bacteria: *Escherichia coli* AJ 11882 (FERM-P 6517=FERM-BP 136, etc.)
  (b) molecular weight: 6.6 megadaltons
  (c) restriction map of restriction enzyme: see FIG. 1
  (d) properties: composite plasmid of pAM 330 and pBR 325 (*Gene*, 4, 121 (1978)), transmitter of chloramphenicol resistance;
(4) pAJ 611:
  (a) host bacteria: *Escherichia coli* AJ 11884 (FERM-P 6519=FERM-BP 138, etc.)
  (b) molecular weight: 6.6 megadaltons
  (c) restriction map of restriction enzyme: see FIG. 2
  (d) properties: composite plasmid of pAM 281 and pBR 325, transmitter of chloramphenicol resistance;
(5) pAJ 440:
  (a) host bacteria: *Baccilus subtilis* AJ 11901 (FERM-BP 140=ATCC 39139, etc.)
  (b) molecular weight: 6.0 megadalton
  (c) restriction map of restriction enzyme: see FIG. 3
  (d) properties: composite plasmid of pAM 330 and pUB 110 (*Bacteriol.*, 134, 318 (1978)), transmitter of kanamycin resistance;
(6) pAJ 1844:
  (a) host bacteria: *Escherichia coli* AJ 11883 (FERM-P 6519=FERM-BP 137, etc.)
  (b) molecular weight: 5.4 megadalton
  (c) restriction map of restriction enzyme: see FIG. 4
  (d) properties: composite plasmid of pHM 1519 and pBR 325, transmitter of chloramphenicol resistance; and
(7) pAJ 3148:
  (a) host bacteria: *Corynebacterium glutamicum* SR 8203 (ATCC 39137, etc.)
  (b) molecular weight: 6.6 megadaltons
  (c) restriction map of restriction enzyme: see FIG. 5
  (d) properties: composite plasmid of pHM 1519 and pUB 110, transmitter of kanamycin resistance.

Other examples of plasmids capable of propagating in cells of Coryneform bacteria include pCG 1 (Japanese Published Unexamined Patent Application No. 57-134500), pCG 2 (Japanese Published Unexamined Patent Application No. 58-35197), pCG 4, pCG 11 (Japanese Published Unexamined Application No. 57-183799). All such plasmids are employable in the practice of this invention.

The vector DNA is cleaved by the same restriction enzyme used for cleavage of the chromosomal gene or is connected to an oligonucleotide having a complementary base sequence at the respective terminals of the chromosomal DNA cleavage fragment and the cleaved vector DNA. The plasmid vector and the chromosomal gene-containing fragment are then subjected to a ligation reaction. When a gene is inserted by this or any other method in the sense direction and in proper reading frame so that the PEPC enzyme is expressed when the plasmid is transcribed and translated by the genetic machinery of a cell in which the plasmid is inserted, the gene is said to be "operationally inserted" into the plasmid vector.

The incorporation of the thus-obtained recombinant DNA comprising the chromosomal DNA and the vector plasmid into recipients belonging to Coryneform and Brevibacterium bacteria can be accomplished by a method which comprises treating the recipient cells with calcium chloride to increase the permeability of DNA, as is reported regarding *Escherichia coli* K-12 (Mandel, M. and Higa, A., *J. Mol. Biol.*, 53, 159 (1970)), or by a method which comprises incorporating DNA at a particular stage of growth (so-called competent cells) when cells become capable of incorporating DNA, as is reported for *Bacillus subtilis* (Duncan, C. H., Wilson, G. A. and Young, F. E., *Gene*, 1, 153 (1977)). The plasmids can also be incorporated into the DNA recipients by forming protoplasts or spheroplasts of the DNA recipients which easily incorporate plasmid DNA, as is known for *Bacillus subtilis*, Actinomycetes and yeast (Chang, S. and Cohen, S. N., *Molec. Gen. Genet.*, 168, 111 (1979); Bibb, M. J. Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978).

In the protoplast method, a sufficiently high frequency can be obtained even by the method used for *Bacillus subtilis* described above. Further, there can be properly used a method described in Japanese Published Unexamined Patent Application No. 57-183799, which comprises incorporating DNA into protoplast of the genus Corynebacterium or the genus Brevibacterium in the presence of polyethylene glycol or polyvinyl alcohol and divalent metal ions. Equivalent effects can also be obtained in various methods of promoting the incorporation of DNA by the addition of carboxymethyl cellulose, dextran, Ficoll, Pluronic F68 (Celva Company), etc., instead of polyethylene glycol or polyvinyl alcohol.

To obtain PEPC-deficient strains, glutamic acid auxotrophs are isolated, since the pathway via PEPC is a main pathway for metabolism of organic acids in the TCA (Tricarboxylic acid) cycle. More specifically, among the glutamic acid auxotrophs, the PEPC-deficient strains can be obtained as strains which cannot grow on a minimum medium containing 5 µg/l of biotin but grow on a medium containing 500 µg/l of biotin.

After transformation, bacterial strains that acquire PEPC productivity or express other properties further possessed by the plasmid vectors as markers are isolated as the desired transformants. Such transformants carry the recombinant DNAs harboring the PEPC gene. To isolate the recombinant DNA, for example, bacteria are lysed by treatment with lysozyme and sodium dodecyl sulfate (SDS). After treatment with phenol, a 2-fold volume of ethanol is added to thereby precipiate and recover DNAs.

In many cases, the PEPC-deficient strains carrying the aforesaid recombinant DNAs produce a variety of amino acids by themselves. In order to obtain amino acid-producing bacteria having high productivity, however, transformation with the recombinant DNA may be done using strains already having high productivity of desired amino acids. Representative examples of such recombinant DNA recipients include the following: auxotrophs for homoserine when lysine-producing bacteria are the target organism; 2-thiazolealanine-resistant bacteria in the production of arginine using S-(2-aminoethyl)cysteine resistant strains, etc.; α-amino-β-hydroxyvaleric-acid-resistant strains in the production of threonine; α-amino-β-hydroxyvaleric-acid resistant strains in the production of isoleucine; 2,4-dehydroproline-resistant strains in the production of proline; and keto-maleic-acid-tolerant strains in the production of glutamic acid, etc.

The methods of culturing the L-amino-acid-producing bacteria thus obtained are conventional and are similar to the methods for the cultivation of conventional L-amino-acid-producing bacteria. That is, the culture medium can be a conventional medium containing carbon sources, nitrogen sources, and inorganic ions and, when required, minor organic nutrients such as vitamins and amino acids. Examples of carbon sources include glucose, sucrose, lactose and starch hydrolysates containing them; Whey; molasses; etc. Examples of nitrogen sources include gaseous ammonia, aqueous ammonia, ammonium salts and other nitrogen-containing inorganic and organic compounds.

Cultivation is conducted under aerobic conditions in which the pH and the temperature of the medium are adjusted to a suitable level, and cultivation is continued until the formation and accumulation of L-amino acids cease.

Thus, markedly high amounts of L-amino acids are formed and accumulated in the culture medium. To recover L-amino acids from the culture medium, any of the known conventional manners is applicable.

In addition to the above general procedures which can be used for preparing amino-acid-producing bacteria in accordance with the practices of this invention, other known techniques and modifications thereof can be used in carrying out the practice of the invention. In particular, techniques relating to genetic engineering have recently undergone exclusive growth and development. Many recent U.S. patents disclose plasmids, genetically engineered microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified by utilizing a PEPC gene in place of the gene described specifically in the patents.

All of these patents as well as all other patents and other publications cited in this disclosure are indicative of the level of skill of those skilled in the art to which this invention pertains and are all herein incorporated by reference.

The invention now being generally described, the same will be better understood by reference to certain specific examples which are included herein for purposes of illustration only and are not intended to be limiting of the invention or any embodiment thereof, unless specified.

EXAMPLE (1) Preparation of chromosomal DNA carrying a PEPC gene

*Brevibacterium lactofermentum* ATCC 13869 was inoculated on 1 liter of CMG (complete medium-glucose) medium (peptone 1 g/dl, yeast extract 1 g/dl, glucose 0.5 g/dl and NaCl 0.5 g/dl; adjusted pH to 7.2) and subjected to shake culture at 30° C. for about 3 hours to harvest cells at an exponential growth phase. After the cells were lysed by lysozyme and SDS, chromosomal DNAs were extracted and purified by conventional treatment using phenol to finally obtain 3.5 mg of DNAs.

(2) Preparation of vector DNA

Using pAJ 43 (molecular weight, 3.4 megadaltons) as a vector, its DNAs were prepared from pAJ 655 and pBR 325 as follows:

Plasmid pAM 330 was obtained by culturing *Brevibacterium lactofermentum* ATCC 13869 (at a temperature of 30° C. in a CMG medium (pH 7.2) containing, per 1 liter of distilled water, 10 g of peptone, 10 g of powdered yeast exract, 5 g of sodium chloride and 5 g of glucose) to reach a later exponential growth phase, at which time the cells were harvested. After the thus-obtained cells were lysed by the conventional method for lysing with lysozyme and SDS, the lysed cells were centrifuged at 30,000 x g for 30 minutes to obtain 64 ml of the supernatant. Plasmid DNAs in the supernatant were precipitated by adding polyethylene glycol (final concentration 10%) to the supernatant and then dissolved in 10 ml of a Tris-EDTA-NaCl (TEN) buffer solution.

After treating DNAs with ribonuclease (reacted with 150 μg/ml of ribonuclease at 37° C. for 30 minutes), DNAs were extracted with phenol. Then, a 2-fold volume of ethanol was added thereto to precipitate DNAs at −20° C. The precipitates were dissolved in 1 ml of a TEN buffer solution. The DNA solution was subjected to agarose gel electrophoresis. From the gel, about 74 μg of pure plasmid DNAs were isolated.

Plasmid pAJ 655 was prepared as follows. One unit of restriction enzyme BamH I (purchased from Bethesda Research Laboratories BRL) was reacted with 0.2 μg of plasmid pBR 325 (Boliver, F., *Gene*, 4, 121 (1978), purchased from BRL) at 37° C. for 60 minutes to thoroughly decompose its DNAs.

Restriction enzyme Mbo I, 0.2 unit, was reacted with 1.2 μg of plasmid pAM 330 at 37° C. for 15 minutes to partially decompose its DNAs.

The thus-obtained DNA fragments were mixed, and the mixture was heat-treated at 65° C. for 10 minutes to inactivate the restriction enzyme. Thereafter, 0.01 unit of T$_4$ DNA ligase was reacted with the DNA fragments at 22° C. for 2 hours in the presence of ATP and dithiothreitol. T$_4$ DNA ligase was inactivated by treatment at 65° C. for 10 minutes. After a 2-fold volume of ethanol was added thereto, DNAs were recovered by centrifugation at 15,000 g for 15 minutes. The thus-obtained composite plasmids were used for transformation.

*Escherichia coli* C-600 (thr$^-$, leu$^-$, thiamine$^-$, r$^-$, m$^-$) (*Meselson, M. and Yuan, R., Nature,* 217, 1110 (1968)) was cultured in 20 ml of a CMG medium at 30° C. to reach a medium exponential growth phase, at which time the cells were harvested. Using the obtained DNAs, C-600 was transformed in accordance with the method of Kushner et al. [*Genetic Engineering,* p. 17 (1978), Elsevier/North Holland Biomedical Press).

The transformants were cultured at 37° C. for 24 hours in a CMG medium containing 20 μg/ml of chloramphenicol and selected. From the transformants, AJ 11882 (FERM-BP 136) was selected and used in the following experiment.

The composite plasmid pAJ 655 was isolated from the lysate of AJ 11882 by the following method: After culturing AJ 11882 in a CMG medium, it was lysed by the conventional method of Tanaka et al., *J. Bacteriol.,* 121, 354 (1975). The lysate was applied to an agarose gel and electrophoresed (Sharp et al., *Biochemistry,* 12, 3055 (1973)). By comparison with a molecular weight marker, the molecular weight of the plasmid was determined to be 6.6 Md. A restriction map of the plasmid is shown in FIG. 1. It was confirmed by the method of K. J. Danna (*Methods in Enzymology,* 65, 499, Academic Press (1980)) that the plasmid was constructed with the pBR 325 fragment and the pAM 330 fragment.

The plasmid pAJ43 was prepared from pAJ 655 as follows:

*Brevibacterium lactofermentum* No. 64 carrying pAJ 655 could not grow on CMG agar medium (peptone 10 g/l, yeast extract 10 g/l, glucose 5 g/l NaCl 5 g/l and agar 20 g/l, adjusted pH to 7.2) containing 100 μg/ml of chloramphenicol. However, a strain resistant to 100 μg/ml of chloramphenicol was obtained by culturing the bacteria in CMG medium, further culturing them at 30° C. in CMG liquid medium containing 100 μg/ml of chloramphenicol overnight, then spreading a suitable amount onto CMG medium containing the same concentration of chloramphenicol, and finally culturing at 30° C. for 1 to 2 days. Examination of this strain in terms of chloramphenicol resistance showed resistance up to 200 μg/ml.

From the high-concentration-chloramphenicol-resistant transformants obtained as the above results, pAJ 43 DNA was prepared as follows. Firstly, this strain was inoculated on 1 liter of CMG liquid medium containing 10 μg/ml of chloramphenicol and cultured at 30° C. to reach a late exponential growth phase, at which time the cells were harvested. After the cells were lysed by lysozyme and SDS in a conventional manner, they were supercentrifuged at 30,000×g for 30 minutes to obtain the supernatant. Polyethylene glycol (final concentration 10%) was added to the supernatant to precipitate DNAs. After concentration, the precipitates were dissolved in 10 ml of tris/EDTA/NaCl buffer. After treating DNAs with ribonuclease (reacted with 150 μg/ml of ribonuclease at 37° C. for 30 minutes), DNAs were extracted with phenol. Then a 2-fold volume of ethanol was added to precipitate DNAs at −20° C. The precipitates were dissoved in 1 ml of tris-/EDTA/NaCl buffer. The DNA solution was applied to agarose gel electrophoresis (voltage: 5 V per 1 cm of gel, 15 hours) to fractionate and harvest 150 μg of pure pAJ 43 plasmid.

The properties of pAJ 43 DNA are as follows:

The molecular weight of pAJ 43 was determined by agarose gel electrophoresis. Agarose gel electrophoresis was conducted by moving with 5 V for 15 hours, per cm of gel length, at a constant voltage, using 0.8% gel, in accordance with the method of Sharp et al (*Biochemistry,* 12, 3055 (1973)). The molecular weight was determined as 3.4 Md by reacting 0.5 μg of pAJ 43 with 0.5 unit of restriction enzyme Hind III— which cleaves pAJ 43 at one position—at 37° C. for 1 hour, cleaving to render pAJ 43 linear and then calculating the molecular weight by comparison of the mobility with that of a molecular weight marker, Hind III fragment (purchased from BRL) of λ phage, having known molecular weight.

Figure 6:
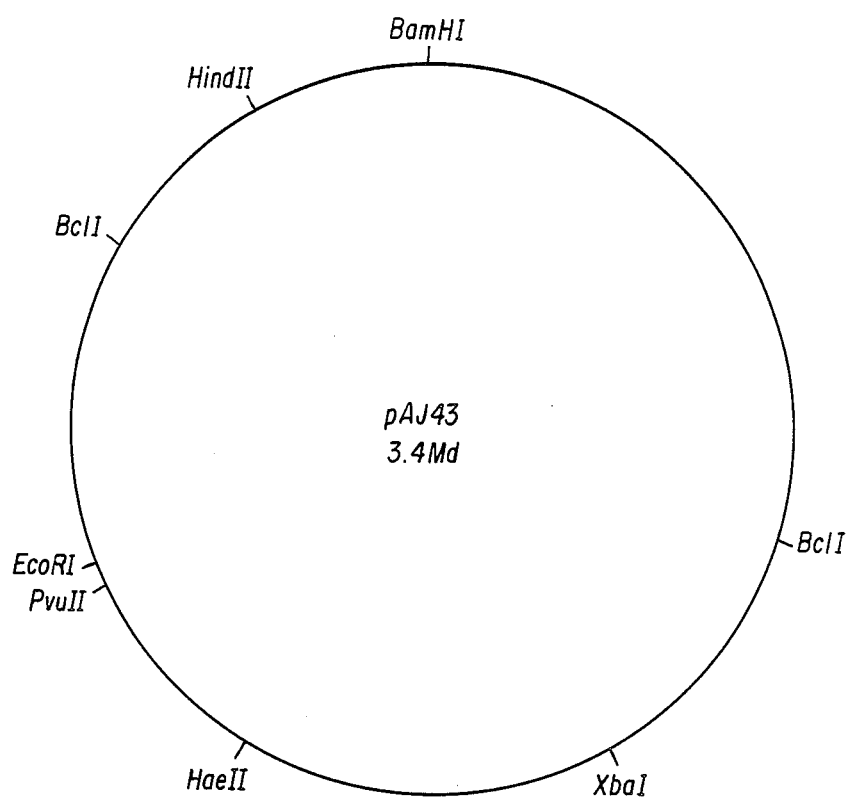
FIG. 6 is a restriction map of composite plasmid pAJ 43.

Preparation of restriction map of pAJ 43 DNA:

A commercially available group of restriction enzymes from BRL was used, and cleavage of pAJ 43 DNA with the restriction enzyme was performed under the conditions indicated for respective enzymes, using at least a 3-fold excess amount of enzyme. When plasmid DNA was cleaved with at least one restriction enzyme for purpose of preparing a restriction map, a fragment cleaved with the first restriction enzyme was isolated by the method of Tanaka et al (T. Tanaka., B. Weisblum, *J. Bacteriol.,* 121, 354 (1975)) from agarose gel, then concentrated by precipitation with ethanol, and cleaved with a second restriction enzyme. The cleaved fragments were applied to agarose gel electrophoresis by the method of Example 3 to calculate the molecular weights. The restriction map shown in FIG. 6 was thus prepared. From the results, it can be seen that pAJ 43 was a small plasmid consisting of a fragment of about 1 Md carrying a chloramphenicol-resistant genetic region of pBR 325 formed from pAJ 655 by deletion in vivo and a fragment of about 2.4 Md carrying a region essential for replication and maintenance of pAM 330.

Measurement of copy number of pAJ 43:

*Brevibacterium lactofermentum* No. 64 (AJ 11997, FERM-P 6857) for maintaining pAJ 43 was inoculated on 5 ml of CMG liquid medium containing 10 μg/ml of chloramphenicol followed by cultivation at 30° C. overnight. Aliquots (0.1 ml) of the culture liquid were again inoculated on 5 ml of CMG liquid medium containing 10 μg/ml of chloramphenicol. The cultivation was continued at 30° C. to reach an early exponential growth phase. After adding ampicillin to a concentration of 1000 μg/ml, the cultivation was continued for a further 2 hours. The cells were harvested by centrifugation and suspended in 1.5 ml of tris/EDTA/NaCl buffer containing 10 mg/ml lysozyme. After incubation at 37° C. for 2 hours, SDS (final concentration 4%) was added to lyse at 65° C. for 20 minutes. After confirming that protoplasts were fully lysed, extraction was performed with phenol. Then a 2-fold volume of ethanol was added to the extract to precipiate DNAs at −20° C. The precipitates were suspended in a small amount of tris/EDTA/NaCl buffer. After treating the DNA solution with ribonuclease (reacted with 150 μg/ml of ribonuclease at 37° C. for 60 minutes), extraction was again performed with phenol. Then, a 2-fold volume of ethanol was added to precipitate DNA at −20° C. The precipitates were suspended in a small amount of tris-/EDTA/NaCl buffer. The suspension was subjected to 0.8% agarose gel electrophoresis. A negative film of the electrophoresis was applied to a densitometer to determine the proportion of chromosomal DNAs to plasmid DNAs. The molecular weights of chromosomal DNAs and plasmid DNAs were determined as $3.0 \times 10^9$ daltons and $3.4 \times 10^6$ daltons. The copy number was determined by calculation and found to be 24 copies per chromosome. The copy number of pAJ 655 calculated in a similar manner was found to be 11 copies, and it was noted that the copy number was doubled by miniaturization.

(3) Insertion of chromosomal DNA fragment into vector

Chromosomal DNAs, 20 μg, obtained in (1) and 10 μg of plasmid DNAs were treated at 37° C. for 1 hour with the restriction endonuclease Hind III, respectively, to fully cleave them. After heat treatment at 65° C. for 10 minutes, both reaction liquids were mixed, and the mixture was subjected to a ligation reaction between the DNA chains with DNA ligase derived from $T_4$ phage at 10° C. for 24 hours in the presence of ATP and dithiothreitol. After heat treatment at 65° C. for 5 minutes, a 2-fold volume of ethanol was added to the reaction liquid to precipitate and harvest DNAs produced by the ligation reaction.

(4) Cloning of PEPC gene

Brevibacterium lactofermentum (AJ 12061) in which the PEPC activity was reduced to 50% was used as a recipient.

As a method for transformation, the protoplast transformation method was used. Firstly, the strain was cultured in 5 ml of CMG liquid medium to reach an early exponential growth phase. After adding 0.6 unit/ml of penicilline G thereto, shake culture was performed for further 1.5 hour. The cells were harvested by centrifugation and washed with 0.5 ml of SMMP medium (pH 6.5) composed of 0.5M sucrose, 20 mM maleic acid, 20 mM magnesium chloride and 3.5% Penassay broth (Difco). Then, the cells were suspended in SMMP medium containing 10 mg/ml of lysozyme to cause protoplastation at 30° C. for 20 hours. After centrifugation at 6000×g for 10 minutes, the protoplasts were washed with SMMP and resuspended in 0.5 ml of SMMP. The thus-obtained protoplasts were mixed with 10 μg of DNAs prepared in (3) in the presence of 5 mM EDTA. After polyethylene glycol was added to the mixture to reach a final concentration of 30%, the mixture was allowed to stand for 2 minutes at room temperature to incorporate DNAs into the protoplasts. After washing the protoplasts with 1 ml of SMMP medium, the protoplasts were resuspended in 1 ml of SMMP medium. The suspension was incubated at 30° C. for 2 hours to effect phenotypic expression. The culture liquid was spread on protoplast regeneration medium of pH 7.0. The protoplast regeneration medium contained, per one liter of distilled water, 12 g of tris(hydroxymethyl)aminomethane, 0.5 g of KCl, 10 g of glucose, 8.1 g of $MgCl_2 . 6H_2O$ 2.2 g of $CaCl_2 . 2H_2O$, 4 g of peptone, 4 g of powdered yeast extract, 1 g of Casamino acid (Difco Company), 0.2 g of $K_2HPO_4$, 10 g of glutamic acid, 500 μg of biotin, 135 g of sodium succinate, 8 g of agar and 3 μg/ml of chloramphenicol.

After cultivation at 30° C. for 2 weeks, approximately 500 colonies resistant to chloramphenicol appeared, which were replicated in a glutamic-acid-free medium (Glu-deficient medium: 2% glucose, 1% ammonium sulfate, 0.25% urea, 0.1% dihydrogen potassium phosphate, 0.04% magnesium sulfate heptahydrate, 2 ppm iron ions, 2 ppm manganese ions, 200 μg/l thiamine hydrochloride and 5 μg/l biotin; pH 7.0, agar 1.8%) to obtain a strain resistant to chloramphenicol and having lost auxotrophy for glutamic acid. This strain was named AJ 12066 (FERM-P 7176).

(5) Plasmid analysis of the transformant

Figure 7:
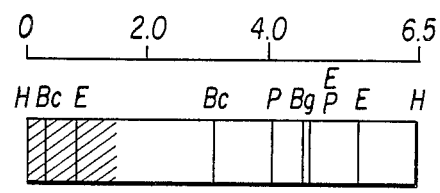
FIG. 7 is a restriction map of composite plasmid pAJ 200.

AJ 12066 was treated in a manner described in (2) to prepare the lystate. Plasmid DNAs were detected by agarose gel electrophoresis. Plasmids having a molecular weight of 10.5 megadaltons obviously larger than that of vector pAJ 43 were detected. The recombinant plasmids were named pAJ 200. A restriction map of pAJ 200 is shown in FIG. 7.

(6) Retransformation

In order to confirm that the PEPC gene was present on the recombinant plasmid containing the DNA fragment of 7.1 megadaltons detected in (5), Brevibacterium lactofermentum AJ 12061 was retransformed using this plasmid DNA.

From each of the thus-formed chloramphenicol-resistant colonies, 30 strains were selected. Examination of auxotropy for glutamic acid indicated that the auxotrophy was recovered in all of the colonies, and it became clear that the PEPC genes were present on the recombinant plasmids described above.

(7) Collection of strain carrying stabilized plasmid and plasmid analysis

Figure 8:
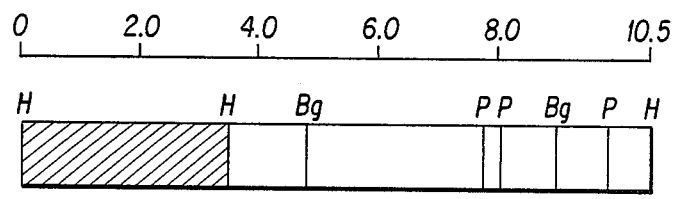
FIG. 8 is a restriction map of composite plasmid pAJ 201.

The plasmids described above were very unstable. A strain carrying miniaturized, stable plasmids was therefore prepared. In protoplast transformation of Coryneform bacteria, introduction of a plasmid having a large molecular weight sometimes results in partial omission of the DNA chains to cause miniaturization of the plasmid. As the result of examination of plasmids on 100 retransformants, miniaturized plasmids were detected in 8 strains. These miniaturized plasmids were stably maintained in the strains. From one of the strains, plasmids were prepared in high amounts, which were named pAJ 201. A restriction map of pAJ 201 is shown in FIG. 8.

(8) Enzyme activity of transformants

Transformant AJ 12065 (FERM-P 7175), recipient AJ 12061 and wild strain ATCC 13869, which was an original strain of them, were shake cultured for 48 hours in glutamic-acid-producing medium (glucose, 8 g/dl; $KH_2PO_4$, 0.1 g/dl; $MgSO_4 . 7H_2O$, 0.1 g/dl; $FeSO_4 . 7H_2O$, 0.001 g/dl; $MnSO_4. 4H_2O$, 0.001 g/dl; urea, 0.4 g/dl; thiamine hydrochloride, 200 μg/l; biotin, 3 μg/l and soybean hydrolysate, 36 mg/dl as total nitrogen; adjusted to pH 6.8), while adjusting pH by the urea addition method. The thus-obtained cells were suspended in tris buffer of pH 7.5 containing 0.1 M ammonium sulfate. After ultrasonic treatment, the suspension was centrifuged at 32,000×g for 30 minutes to obtain the supernatant. The supernatant was treated with ammonium sulfate to remove low molecular weight substances. The PEPC activity was measured with the supernatant using an enzyme reaction liquid composed of 100 mM tris hydrochloride (pH 7.5), 2 mM phosphoenol pyruvic acid, 3.3 mM $MnSO_4$, 10 mM $NaHCO_3$, 0.1 mM acetyl CoA, 0.15 mM NADH and 10 μg malate dehydrogenase. The reaction was performed in a colorimetric cell. Incremental oxaloacetic acid production was quantitatively assayed by determining the rate of decrease of NADH by measuring the extinction coefficient at 366 nm.

The results are shown in Table 1.

TABLE 1

| Strain | Specific Activity of PEPC n mol/min/mg.protein | Specific Activity (%) |
| --- | --- | --- |
| ATCC 13869 | 407 | 100 |
| AJ 12061 | 308 | 76 |
| AJ 12065 | 685 | 168 |

(g) Productivity of glutamic acid by the transformant

Plasmid pAJ 201 was introduced into *Brevibacterium lactofermentum* ATCC 13869 and *Corynebacterium glutamicum* ATCC 13060 by the transformation method described in (4), and transformants were selected utilizing chloramphenicol resistance as a marker. The thus-obtained AJ 12062 (FERM-P 7172) induced from *Brevibacterium lactofermentum* ATCC 13869 and AJ 12067 (FERM-P 7177) induced from *Corynebacterium glutamicum* ATCC 13060 were cultured to examine glutamic acid productivity. The results shown in Table 2 were obtained. The cultivation was carried out by charging in a shoulder-equipped flask 20 ml of medium containing 10 g/dl of glucose, 0.1 g/dl of $KH_2PO_4$, 0.1 g/dl of $MgSO_4 \cdot 7H_2O$ 0.001 g/dl of $FeSO_4 \cdot 4H_2O$, 0.001 g/dl of $MnSO_4 \cdot 4H_2O$, 36 mg/dl of soybean protein hydrolysate (as total nitrogen), 200 μg/l of thiamine hydrochloride, 3 μg/l of biotin, 4.5 g/dl (2.5 g/dl) of $(NH_4)_2SO_4$, 5 g/dl of calcium carbonate and 10 μg/ml of chloramphenicol (used in the case of the transformant), the pH of which had been adjusted to 7.0 (KOH), while shaking at 31.5° C. for 72 hours. After completion of the cultivation, glutamic acid in the culture liquid was quantitatively determined with an autoanalyzer for glutamic acid.

TABLE 2

| Strain | Amount of Glutamic Acid Produced (g/dl) |
| --- | --- |
| ATCC 13869 | 5.04 |
| AJ 12062 | 5.34 |
| ATCC 13060 | 4.50 |
| AJ 12067 | 4.65 |

(10) Productivity of lysine with the transformant

Plasmid pAJ 201 was introduced into *Brevibacterium lactofermentum* AJ 12019 (NRRL B-15346) (auxotrophy for homoserine) by the transformation method described in (4). The results obtained by examination of lysine productivity with the thus-obtained transformant AJ 12073 (FERM-P 7205) are shown in Table 3. The cultivation was carried out by charging in a shoulder-equipped flask 20 ml of medium containing 10 g/dl of glucose, 5.5 g/dl of ammonium sulfate, 0.1 g/dl of $KH_2PO_4$, 0.1 g/dl of $MgSO_4 \cdot 0.001$ g/dl of $FeSO_4 \cdot 4H_2O$, 0,001 g/dl of $MnSo_4 \cdot 4H_2O$, 200 μg/l of thiamine hydrochloride, 2.5 mg/dl of nicotinamide, 105 mg/dl of soybean protein hydrolysate (as total nitrogen), and 5 g/dl of calcium carbonate, the pH of which had been adjusted to 8.0, while shaking at 31.5° C. for 72 hours.

After completion of the cultivation, lysine in the culture liquid was quantitatively determined with high speed liquid chromatography.

TABLE 3

| Strain | Amount of Lysine Produced (g/dl) |
| --- | --- |
| AJ 12019 | 1.5 |
| AJ 12073 | 1.9 |

(11) Productivity of proline with the transformant

Plasmid pAJ 201 was introduced into *Brevibacterium lactofermentum* AJ 11225 (FERM-P 4370) by the transformation method described in (4). The proline productivity was examined with the thus-obtained transformant (AJ 12063 (FERM-P 7173). The results are shown in Table 4. The cultivation was carried out by charging in a shoulder-equipped flask 20 ml of medium containing 10 g/dl of glucose, 6 g/dl of ammonium sulfate, 0.1 g/dl of $KH_2PO_4$, 0.08 g/dl of $MgSO_4 \cdot 7H_2O$, 0.001 g/dl of $FeSO_4 4H_2O$ 0.001 g/dl of $MnSO_4 4H_2O$ 1 mg/l of thiamine hydrochloride, 0.1% of soybean protein hydrolysate ("Mieki"), and calcium carbonate, the pH of which had been adjusted to 7.0, while shaking at 31.5° C. for 72 hours. After completion of the cultivation, proline in the culture liquid was quantitatively determined with high speed liquid chromatography.

TABLE 4

| Strain | Amount of Proline Produced (g/dl) |
| --- | --- |
| AJ 11225 | 1.05 |
| AJ 12063 | 1.80 |

(12) Productivity of threonine with the transformant

Plasmid pAJ 201 was introduced into *Brevibacterium lactofermentum* AJ 11188 (FERM-P 4190) by the transformation method described in (4). Threonine productivity was examined with the thus-obtained transformant AJ 12064 (FERM-P 7174). The results are shown in Table 5. The cultivation was carried out by charging in a shoulder-equipped flask 20 ml of medium containing 10 g/dl of glucose, 4.5 g/dl of ammonium sulfate, 0.1 g/dl of $KH_2PO_4$, 0.1 g/dl of $MgSO_4 \cdot 7H_2O$, 0.001 g/dl of $FeSO_4 4H_2O$, 0.001 g/dl of $MnSO_4 \cdot 4H_2O$, 300 μg/l of thiamine hydrochloride, 100 μg/l of biotin, 45 mg/dl of soybean protein hydrolysate "Mieki" (as total nitrogen), 25 mg/dl of isoleucine, 30 mg/dl of leucine, and 5 g/dl of calcium carbonate, the pH of which had been adjusted to 7.2, while shaking at 31.5° C. for 72 hours. After completion of the cultivation, threonine in the culture liquid was quantitatively determined with high speed liquid chromatography.

TABLE 5

| Strain | Amount of Threonine Produced (g/dl) |
| --- | --- |
| AJ 11188 | 1.54 |
| AJ 12064 | 1.73 |

*Brevibacterium lactofermentum* AJ 12061 was isolated as a strain which could not grow on Glu-deficient medium, but could grow on Glu-deficient medium supplemented with 1.0 g/dl of L-glutamic acid, by contacting *Brevibacterium lactofermentum* ATCC 13869 with N- methyl-N'-nitro-N-nitrosoguanidine at 0° C. for 20 minutes for mutation treatment. AJ 12061, AJ 11225, AJ 11188 and AJ 12019 were easily obtained from AJ 12066 or AJ 12065, AJ 12063, AJ 12064 and AJ 12073, respectively, by removing the composite plasmid without injury to the host cells. That is, the plasmid is spontaneously expelled from the host on some occasions, or it may also be removed by a "removing" operation (*Bact. Rev.*, 36, p 361-405 (1972)). An example of the removing operation is as follows: A small number of cells are inoculated on a medium containing acridine orange having a concentration (2 to 50 μg/ml) insufficiently inhibiting growth of the host so as to be approximately $10^4$ cells per 1 ml. Then the cells are cultured at 27 to 35° C. overnight (*J. Bacteriol.*, 88, 261 (1964)). The culture liquid is spread on agar medium followed by culturing at 27 to 42° C. overnight.

Plasmids would be removed from most of the colonies appearing on the medium with a high degree of probability.

Further, AJ 11225 (resistant to 2,4-dehydroproline) is described in Japanese Published Examined Patent Application 57-22319 and AJ 11188 (resistant to α-amino-β-hydroxyvaleric acid and S-methylcysteine sulfoxide and showing auxotrophy for L-isoleucine and L-leucine) is described in Japanese Published Examined Patent Application No. 56-3038.

The deposits identified as FERM-p numbers 6857, 7176, 7175, 7177, 7172, 7205, 7173,, and 7174 were converted on August 21, 1984, to deposits under the Budapest Treaty and are identified by the FERM-BP numbers 591 , 590 , 589 , 588 , 587 586 , 585 , and 592 , respectively.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A recombinant DNA molecule comprising a plasmid and a gene coding for phosphoenol pyruvate carboxylase operationally inserted therein, wherein said recombinant DNA molecule is capable of progapating and said gene is capable of being expressed in a Corynebacterium and Brevibacterium and wherein said gene is a chromosomal gene isolated from a Coryneform strain or a Brevibacterium strain carrying a phosphoenol pyruvate carboxylase, PEPC, gene.

2. A Corynebacterium or Brevibacterium carrying a recombinant DNA molecule comprising a plasimid having operationally inserted therein a gene coding for phosphoenol pyruvate carboxylase, said gene being a chromosomal gene isolataed from a Coryneform strain or a Brevibacterium strain carrying a PEPC gene, wherein said Corynebacterium or Brevibacterium carrying the recombinant DNA molecule expresses both said gene and a chromosomal gene coding for an amino acid.

3. A process for producing an amino acid by fermentation, which comprises:
   cultivating in a culture medium a Corynebacterium or Brevibacterium (1) carrying a recombinant DNA molecule comprising a plasmid having operationally inserted therein a gene coding for phosphoenol pyruvate carboxylase, said gene being a chromosomal gene isolated from a Coryneform strain or a Brevibacterium strain carrying a PEPC gene and (2) having a chromosomal gene coding for said amino acid, and
   isolating said amino acid from said culture medium.

4. A recombinant DNA according to claim 1, wherein said Coryneform strain or Brevibacterium strain from which the gene coding for PEPC is isolate is a strain which exhibits weakened feedback inhibition by aspartic acid.

5. A Corynebacterium or Brevibacerium carrying a recombinant DNA molecule according to claim 2, wherein said Coryneform strain or Brevibacterium strain from which the gene coding for PEPC is isolated is a strain which exhibits weakened feedback inhibition by aspartic acid.

6. A process according to claim 3, wherein said Coryneform strain or Brevibacterium strain from which the gene coding for PEPC is isolated is a strain which exhibits weakened feedback inhibition by aspartic acid.

7. A biologically pure culture of a Corynebacterium or Brevibacterium according to claim 2, which has the identifying characteristics of a member of the group consisting of FERM-BP 591, 590, 589, 588, 587, 586, 585, and 592.

* * * * *